United States Patent
Benett et al.

(10) Patent No.: US 7,413,711 B2
(45) Date of Patent: Aug. 19, 2008

(54) SYSTEM FOR DISPENSING A PRECISE AMOUNT OF FLUID

(75) Inventors: William J. Benett, Livermore, CA (US); Peter A. Krulevitch, Pleasanton, CA (US); Steven R. Visuri, Livermore, CA (US); John M. Dzenitis, Danville, CA (US); Kevin D. Ness, Mountain View, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 567 days.

(21) Appl. No.: 10/621,657

(22) Filed: Jul. 16, 2003

(65) Prior Publication Data

US 2005/0029308 A1 Feb. 10, 2005

(51) Int. Cl.
*B01L 3/02* (2006.01)
(52) U.S. Cl. ............... 422/100; 73/864.13; 73/864.15; 73/864.16
(58) Field of Classification Search ............... 422/100; 73/864.01–864.17
See application file for complete search history.

(56) References Cited

U.S. PATENT DOCUMENTS

| | | | |
|---|---|---|---|
| 3,604,269 A | 9/1971 | Smith et al. | |
| 3,754,443 A | 8/1973 | Harris et al. | |
| 3,824,859 A | 7/1974 | Harris et al. | |
| 4,094,197 A | 6/1978 | Harris et al. | |
| 4,228,922 A | 10/1980 | Takeshita | |
| 4,440,550 A | 4/1984 | Jenkins et al. | |
| 5,540,889 A * | 7/1996 | Gordon et al. | 422/100 |
| 5,756,905 A | 5/1998 | Ueda | |
| 6,257,076 B1 | 7/2001 | Snyder et al. | |
| 2001/0019845 A1* | 9/2001 | Bienert et al. | 436/181 |
| 2002/0043539 A1 | 4/2002 | Pagel et al. | |
| 2002/0114740 A1* | 8/2002 | Yamamoto | 422/100 |
| 2002/0190202 A1 | 12/2002 | Liang | |
| 2004/0076551 A1* | 4/2004 | Saidman et al. | 422/100 |

* cited by examiner

*Primary Examiner*—Jan M Ludlow
(74) *Attorney, Agent, or Firm*—Eddie E. Scott; John H. Lee

(57) ABSTRACT

A dispensing system delivers a precise amount of fluid for biological or chemical processing and/or analysis. Dispensing means moves the fluid. The dispensing means is operated by a pneumatic force. Connection means delivers the fluid to the desired location. An actuator means provides the pneumatic force to the dispensing means. Valving means transmits the pneumatic force from the actuator means to the dispensing means.

3 Claims, 3 Drawing Sheets

SYSTEM FOR DISPENSING A PRECISE AMOUNT OF FLUID

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to dispensing systems and more particularly to a dispensing system for delivering a precise amount of fluid.

2. State of Technology

U.S. Pat. No. 6,257,076 to Philip A. Snyder and James Steven Fullerman issued Jul. 10, 2001 provides the following state of the technology information, "The contributions of the medical, environmental and life sciences to humanity have been facilitated by advances in chemical analysis. Many analytical techniques provide for the division of a complex sample into its components."

U.S. patent application No. 2002/0190202 by Dong C. Liang for a microsample analysis system using dispensing pump and injection port published Dec. 19, 2002 provides the following state of the technology information, "a fully automated chemical analysis system and is particularly well suited for pharmaceutical drug discovery and biomedical research applications (for example, ion channel assays), compromised in part by an electronically controlled microsyringe pump, an injection port, a nebulizer and a FAAS instrument. The different components of the system are connected by tubing, allowing solutions to be exchanged between the various components of the system. The chemical analysis system further includes an autosampler, such as the XYZ autosampler available from Aurora Instruments, an array of sample microplates, and an array of solution containers (for standards, modifiers, buffers, suppressors, etc.)."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a dispensing system for delivering a predetermined precise amount of a fluid for biological or chemical processing and/or analysis. Dispensing means moves the predetermined amount of a fluid for biological or chemical processing and/or analysis. The dispensing means is operated by a pneumatic force. Connection means delivers the predetermined precise amount of a fluid for biological or chemical processing and/or analysis to the desired location. An actuator means provides the pneumatic force to the dispensing means. Valving means transmits the pneumatic force from the actuator means to the dispensing means.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
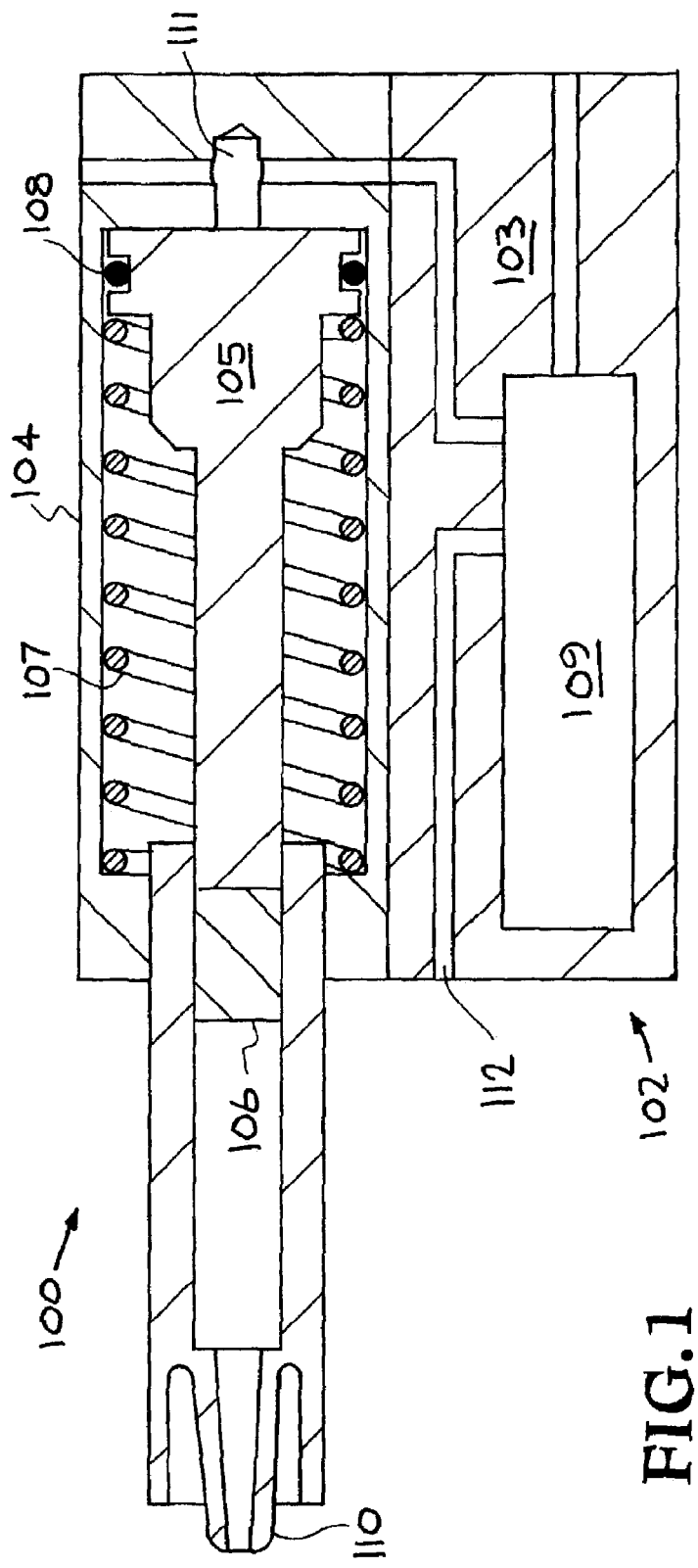
FIG. 1 illustrates a pneumatically actuated dispensing system constructed in accordance with the presenting invention.

Referring now to the drawings, to the following detailed description, and to incorporated materials; detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1, a pneumatically actuated dispensing system constructed in accordance with the presenting invention is illustrated. The dispensing system is designated generally by the reference numeral 100. The dispensing system 100 addresses the increasing need for systems that perform biological or chemical processing and/or analysis. These systems can be complex and can require the dispensing or manipulation of several different liquids or gases for a given process and/or analysis. The dispensing system 100 has uses in systems for performing biological or chemical analysis. Examples include bio-warfare terrorism agent detection, automated laboratory biological and chemical analysis, automated laboratory biological processes, and automated laboratory chemical processes. There is also a growing need for compact systems for automated biological or chemical processes performed in the laboratory and industry. The dispensing system 100 addresses the increasing need for compact systems that are portable or remotely operated and perform biological or chemical processing and/or analysis.

The dispensing system 100 comprises a dispensing component 101, an actuator component 102, and a valving component 103. These components will be described in greater detail below. The dispensing system 100 provides a precise amount of fluid for biological or chemical processing and/or analysis. The dispensing system 100 can be used as an individual dispensing pump to dispense one fluid or gas or can be arranged in an array of dispensing pumps to dispense several or many different liquids or gases. Each individual dispensing system can dispense an appropriate preselected precise volume of liquid or gas.

The Dispensing Component 101—In its simplest form the dispensing component 101 comprises a tube 104 with a rod or plunger 106 and piston 105 that slide down the inside diameter of the tube 104. A spring 107 biases the piston with its associated plunger upward in the tube 104. An "O" ring 108 provides a sliding seal between the piston 105 and the tube 104. The piston 105 is propelled downward by increasing the pressure on one side of the piston 105 with respect to the spring force on the other. This is accomplished by the introduction of pneumatic pressure to one side of the piston 105 through the chamber 111. The piston 105 is attached to the plunger 106 of the dispensing component 101 by a rod or other component thereby creating movement of the plunger 106 with the piston 105. A connection 110 on the tube 104 provides the means for dispensing fluids or gases to the desired unit in the particular process and/or analysis involved. The connection 110 transfers a precise amount of fluid from the tube 104 for biological or chemical processing and/or analysis.

In operation the dispensing component 101 provides a precise volume of liquid or gas to the desired unit in the particular process and/or analysis involved. Actuation of the plunger 106 and piston 105 is created by pneumatic force when a fluid is introduced into the chamber 111. This causes the plunger 106 and piston 105 to slide down the inside diameter of the tube 104 and discharging a precise amount of liquid or gas through the connection 110 to the desired unit in the particular process and/or analysis involved. The precise volume of liquid or gas can be obtained by controlling the diameter of the dispensing body and/or the stroke of the plunger. Changes in the precise volume of liquid or gas can be obtained by varying the diameter of the dispensing body and/or the stroke of the plunger.

Charging the dispensing component 101 is accomplished by the spring 107 forcing the plunger 106 and piston 105 to slide up the inside diameter of the tube 104 and draw in a the desired volume of liquid or gas. The connection 110 is directed to the source of the, particular liquid or gas through an appropriate valve.

The dispensing component 101 can be of almost any size, with volumes from microliters to several milliliters or larger. The dispensing component 101 can be a custom design for a given application or a standard dispensing adapted for pneumatic actuation.

The Actuator Component 102—The actuator component 102 comprises a solenoid valve 109 with an internal solenoid piston sliding in a cylinder. The solenoid piston has a gas tight sliding seal to the walls of the cylinder. The solenoid piston can be either pneumatically powered in both directions by switching the pressure from one side of the solenoid piston to the other and venting the opposite side. It can also be pneumatically powered in one direction and returned by the force of a mechanical spring. A source of pneumatic pressure is introduced through the passage connected to the solenoid valve 109.

The Valving Component 103—The valving component 103 allows the dispensing component 101 to load from one line or source and discharge to another line. This valving component 103 can be controlled electrically or pneumatically. It can also be accomplished by the use of passive check valves.

Figure 2:
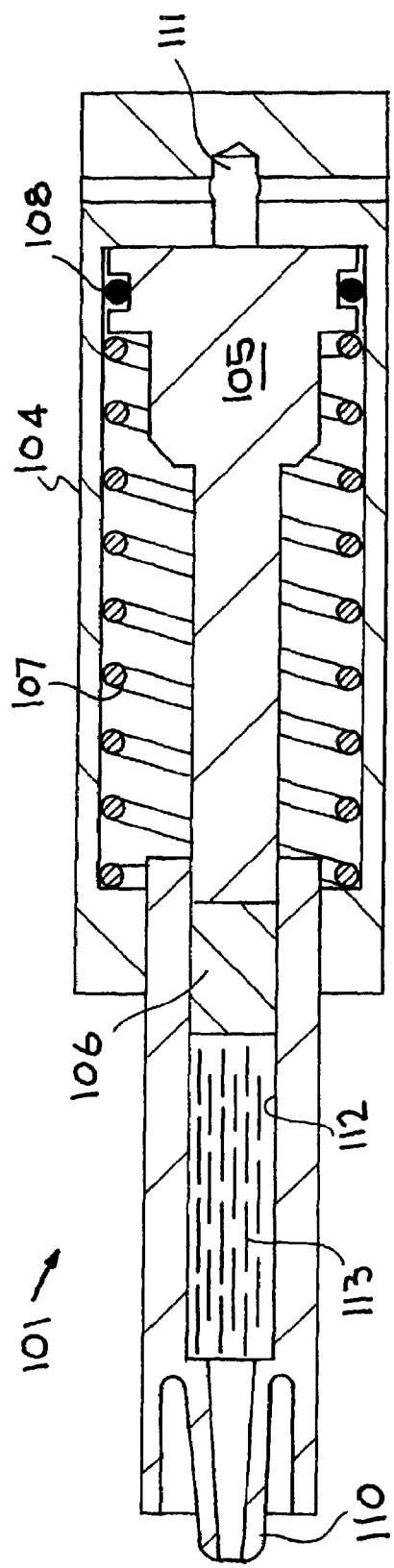
FIG. 2 shows the dispensing component in the loaded position.
Figure 3:
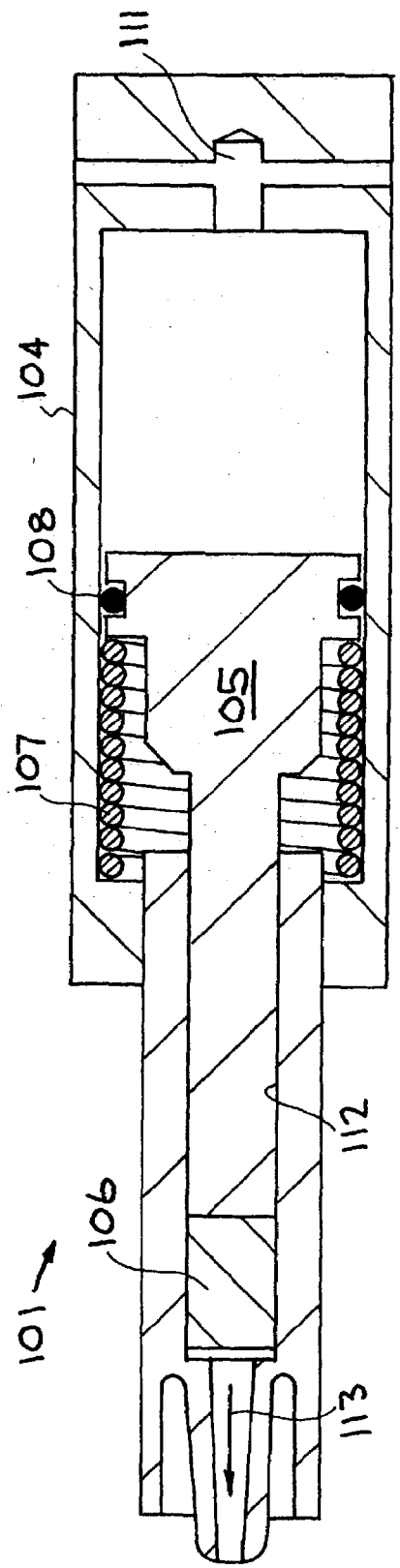
FIG. 3 shows the dispensing component in the discharged position.

Referring now to FIGS. 2 and 3, the operation of the dispensing system 100 will be described. Pneumatic fluid is introduced into the chamber 111 by the valving component 103. A source of pneumatic pressure allows fluid to be introduced into the solenoid valve 109 through the passage connected to the solenoid valve 109. The fluid moves the internal solenoid piston causing it to slide in its cylinder. The solenoid piston has a gas tight sliding seal to the walls of the cylinder. The solenoid piston can be either pneumatically powered in both directions by switching the pressure from one side of the solenoid piston to the other and venting the opposite side. It can also be pneumatically powered in one direction and returned by the force of a mechanical spring. The valving component 103 allows the dispensing component 101 to load from one line or source and discharge to another line. This valving component 103 can be controlled electrically or pneumatically. It can also be accomplished by the use of passive check valves. The passages in the valving component 103 direct the pneumatic fluid into the chamber 112 in the dispensing component 101.

The dispensing component 101 is shown in the loaded position in FIG. 2. The tube 104 contains the desired volume of fluid or gas 113. The connection 110 leads to the desired unit in the particular process and/or analysis involved. Actuation of the plunger 106 and piston 105 is accomplished by introducing a fluid 113 into the chamber 112. This causes the plunger 106 and piston 105 to slide down the inside diameter of the tube 104 and discharge the given volume of fluid or gas 113 through the connection 110.

The dispensing component 101 is shown in the discharged position in FIG. 3. The fluid 113 in the chamber 112 has forced the plunger 106 and piston 105 to slide down the inside diameter of the tube 104. This discharges the desired volume of fluid or gas 113 through the connection 110.

In order to charge the dispensing component 101 with the desired volume of fluid or gas, the pneumatic pressure in chamber 112 is reduced by exhausting chamber 111. The discharging operation has caused the spring 107 to become compressed. Reduction of the pneumatic pressure in chamber 112 allows the force of the spring 107 to forcing the plunger 106 and piston 105 to slide up the inside diameter of the tube 104 and draw in the desired volume of fluid or gas. The connection 110 is directed to the source of the particular fluid or gas through an appropriate valve.

Figure 4:
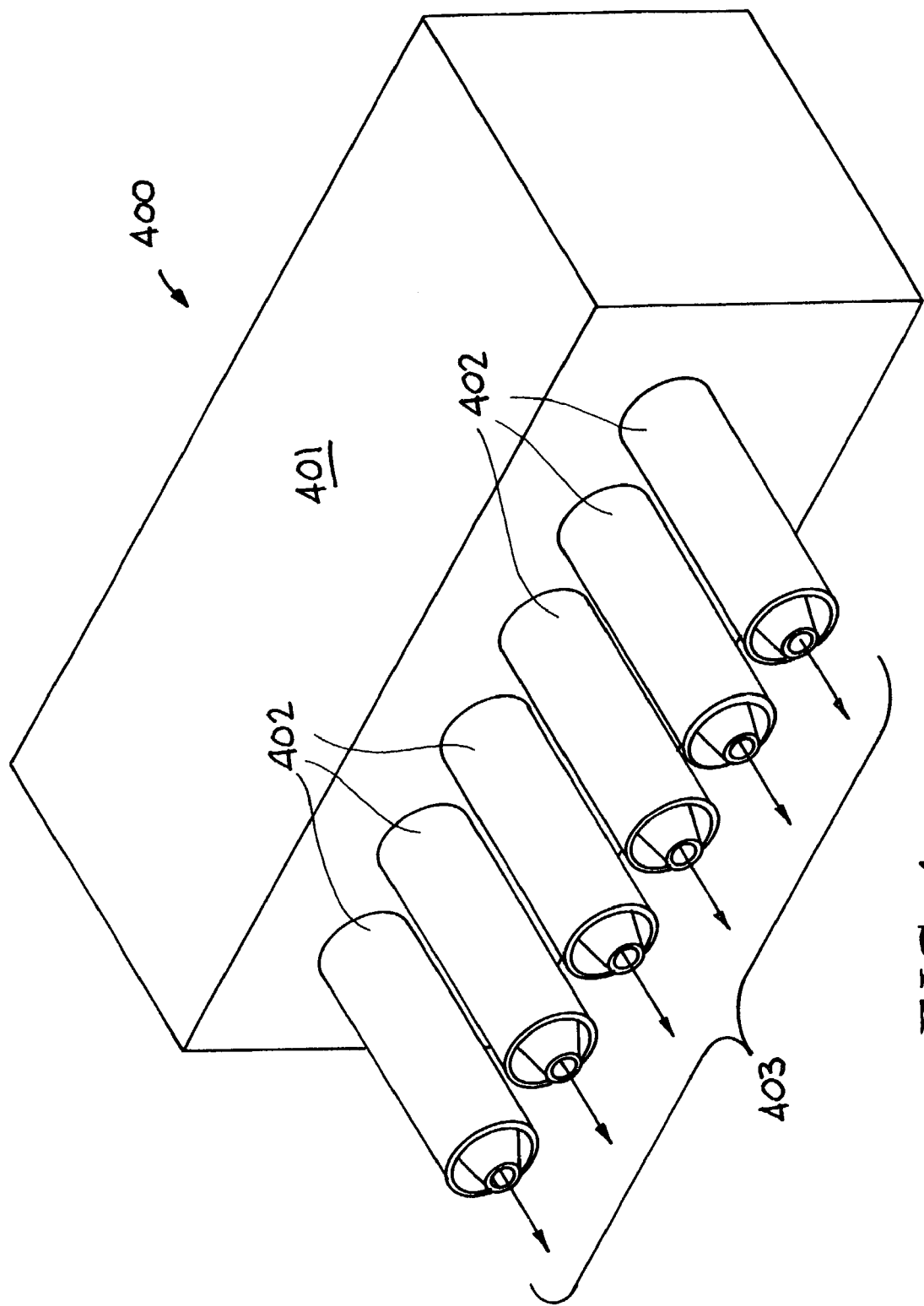
FIG. 4 shows an array of dispensing systems constructed in accordance with the presenting invention.

Referring now FIG. 4, a pneumatically actuated dispensing system array constructed in accordance with the presenting invention is illustrated. The dispensing system array is designated generally by the reference numeral 400. The dispensing system array 400 provides a precise amount of various fluids and/or gases 403 for biological or chemical processing and/or analysis.

A multiplicity of individual dispensing systems 402 are arranged in an array to dispense several or many different fluids or gases 403. The individual dispensing systems 402 are constructed as illustrated in FIGS. 1-3 and described above. The individual dispensing systems 402 are positioned in a body 401. Each individual dispensing system 402 dispenses an appropriate preselected precise volume of liquid or gas 403 to the desired unit in the particular process and/or analysis involved.

The dispensing system array 400 has uses in systems for performing biological or chemical analysis. Examples include bio-warfare terrorism agent detection, automated laboratory biological processes, and automated laboratory chemical processes, automated laboratory biological and chemical analysis.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for delivering a predetermined amount of a fluid for biological or chemical processing and/or analysis, consisting of:
   a tube;
   a piston plunger positioned to slide inside of said tube for dispensing said predetermined amount of a fluid for biological or chemical processing and/or analysis, said piston plunger responsive to a pneumatic force;
   a mechanical device that biases said piston plunger in opposition to said pneumatic force;
   a connector operatively connected to said tube for transferring said predetermined amount of a fluid for biological or chemical processing and/or analysis;
   a chamber directly connected to said tube and open to said piston plunger for directing said pneumatic force directly to said piston plunger,
   an actuator operatively connected to said chamber, said tube and piston plunger for providing said pneumatic force to said piston plunger; and
   valving in said actuator operatively connected to said chamber and said tube and operatively connected to said piston plunger, said valving transmitting said pneumatic force to said chamber, said tube and piston plunger.

2. The apparatus of claim 1 wherein said mechanical device is a spring that biases said piston plunger in opposition to said pneumatic force.

3. A dispensing system for delivering a predetermined amount of a fluid for biological or chemical processing and/or analysis, consisting of:
   dispensing means for moving said predetermined amount of a fluid for biological or chemical processing and/or analysis, said dispensing means operated by a pneumatic force;
   connection means for delivering said predetermined amount of a fluid for biological or chemical processing and/or analysis, said connection means operatively connected to said dispensing means; and
   actuator means for providing said pneumatic force to said dispensing means, said actuator means operatively connected to said dispensing means;
   chamber means directly connected to said dispensing means and open to said actuator means for directing said pneumatic force to said actuator means, and
   valving means in said actuator means for transmitting said pneumatic force to said chamber means and said dispensing means, said valving means operatively connected to said chamber means and said dispensing means,
   wherein said dispensing means is a tube with a piston plunger inside of said tube that slides inside said tube and moves said predetermined amount of a fluid for biological or chemical processing and/or analysis through said connection means, and a biasing spring that biases said piston plunger in opposition to said pneumatic force.

* * * * *